(12) United States Patent
Sander

(10) Patent No.: US 7,382,529 B2
(45) Date of Patent: Jun. 3, 2008

(54) ILLUMINATION APPARATUS, IN PARTICULAR SLIT LAMP

(75) Inventor: Ulrich Sander, Rebstein (CH)

(73) Assignee: Leica Microsystems (Schweiz) AG, Heerbrugg (CH)

(*) Notice: Subject to any disclaimer, the term of this patent is extended or adjusted under 35 U.S.C. 154(b) by 3 days.

(21) Appl. No.: 11/148,734

(22) Filed: Jun. 9, 2005

(65) Prior Publication Data
US 2005/0275939 A1    Dec. 15, 2005

(30) Foreign Application Priority Data
Jun. 11, 2004    (DE) .................... 10 2004 028 471

(51) Int. Cl.
*G02B 21/06* (2006.01)
*A61B 3/10* (2006.01)
(52) U.S. Cl. .................... 359/385; 351/214
(58) Field of Classification Search ................ 359/385, 359/388, 368; 351/214
See application file for complete search history.

(56) References Cited

U.S. PATENT DOCUMENTS

| 4,475,027 | A | * | 10/1984 | Pressley | 219/121.6 |
| 4,932,774 | A | * | 6/1990 | Takagi et al. | 351/221 |
| 5,610,733 | A | * | 3/1997 | Feldman et al. | 359/9 |
| 7,040,765 | B2 | * | 5/2006 | Koest | 353/84 |
| 2005/0024587 | A1 | * | 2/2005 | Somani | 351/214 |

FOREIGN PATENT DOCUMENTS

DE    4227942 C2    3/1993

* cited by examiner

*Primary Examiner*—Alessandro Amari
(74) *Attorney, Agent, or Firm*—Hodgson Russ LLP

(57) ABSTRACT

An illumination apparatus, usable for example as a slit lamp, comprises a light-emitter (2) and an optical element (12) having a free-form surface (13), and optionally a slit aperture (9) and an imaging optic (10). The concept of the present invention is that the free-form surface (13) is employed to generate a resultant illumination beam having a slit-shaped cross-section.

5 Claims, 7 Drawing Sheets

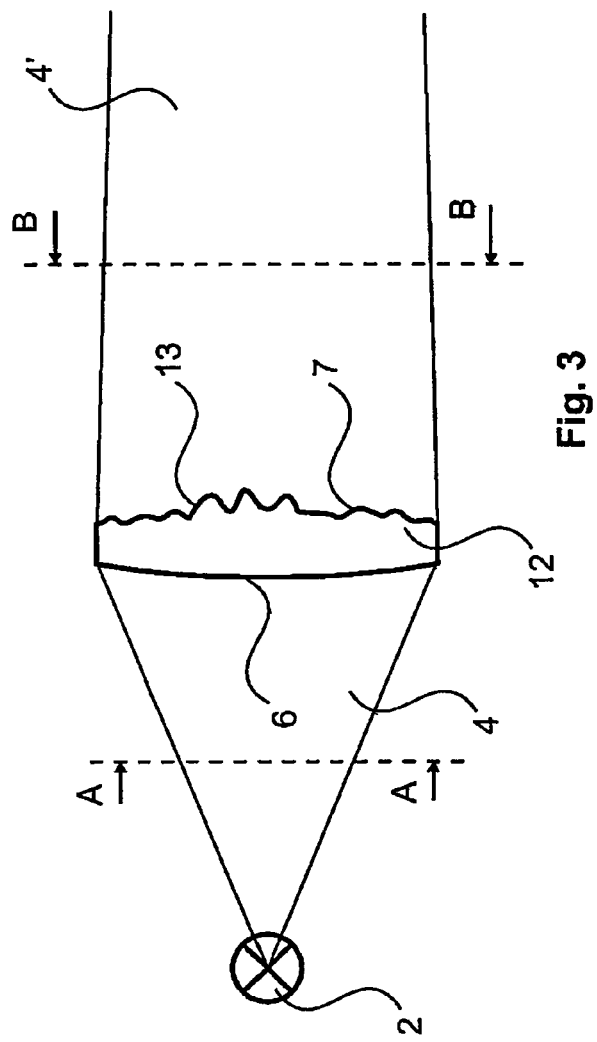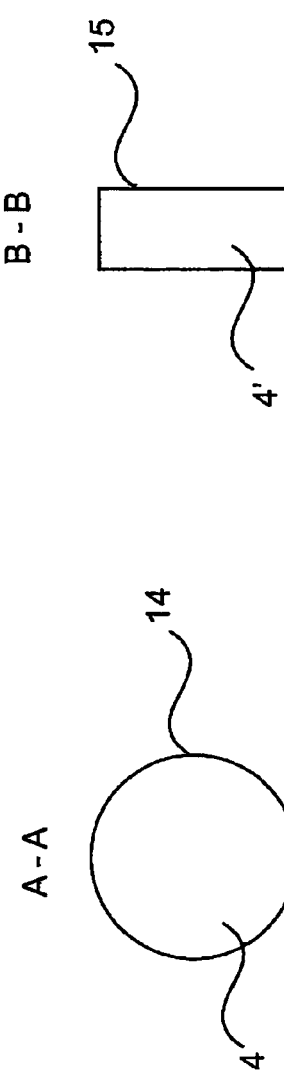

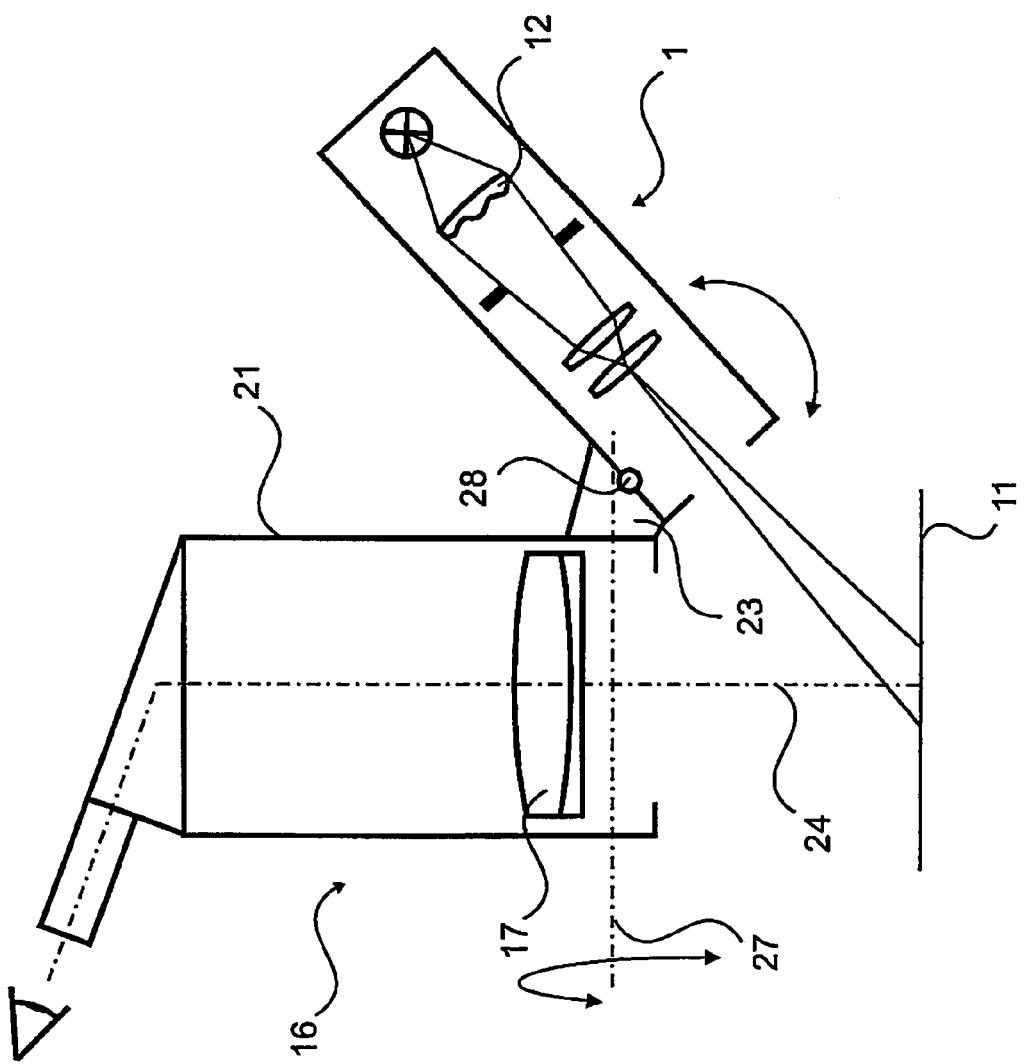
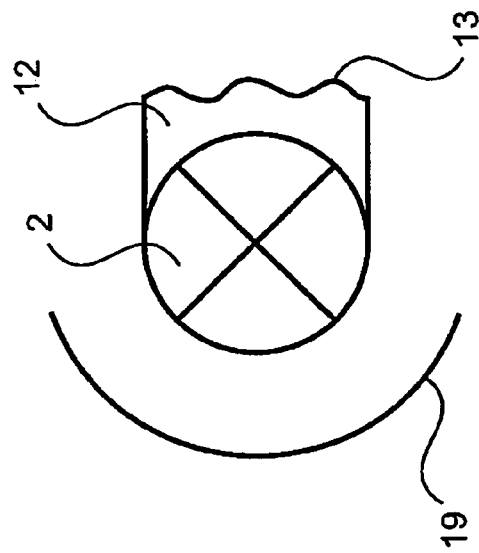
Fig. 7
Fig. 8

ILLUMINATION APPARATUS, IN PARTICULAR SLIT LAMP

CROSS REFERENCE TO RELATED APPLICATIONS

This application claims priority of the German patent application 10 2004 028 471.7 filed Jun. 11, 2004 which is incorporated by reference herein.

FIELD OF THE INVENTION

The invention concerns an illumination apparatus, in particular a slit lamp, that is used for surgery and the diagnosis of certain eye diseases.

BACKGROUND OF THE INVENTION

A "slit lamp" is understood to be a device that is used to observe the front portion of the eye (lens and proximal vitreous body), and to monitor contact lens fittings. The slit image facilitates diagnostic and surgical procedures. During operations, it is used as a contrast-enhancing illumination in the region of the retina.

Slit lamps of this kind are very well known, and are manufactured by several suppliers and used routinely by doctors.

The existing art includes slit lamps in which a slit aperture is illuminated, directly or via a light guide, by means of a light-emitting means. DE-C2-42 27 942, for example, describes an arrangement of a slit lamp with a light guide:

"Slit lamp illumination device for imaging a slit aperture into a target plane, comprising
- a light source, preferably of high intensity, after which is arranged a fiber-optic light guide;
- a slit aperture arranged, without interposed optical elements, at a short distance after the light guide entry surface; and
- a slit aperture arranged, without interposed optical elements, at a short distance after the light guide exit surface; and
- an imaging device arranged after the slit aperture and having at least two optical systems each having a converging optical effect . . . "

In the aforesaid embodiment, a slit aperture is arranged directly after the light guide exit surface. The light guide exit surface, however, has a round cross section. A portion of the light emerging from the light guide illuminates the slit in the plane of the slit aperture. This slit is imaged by an imaging optic onto the patient's eye. A substantially larger portion of the light, however, is absorbed on the mechanical slit aperture and converted into heat, and thus does not contribute to the intensive illumination of the slit image onto the patient's eye.

This conventional embodiment thus creates the problem that because of the transition from the circular surface (exit surface of the light guide) to the rectangular surface (entrance surface of the slit aperture), considerable portions of the usable light from the light guide or from any other light-emitting means are lost.

This problem is not unknown, but the attempts to solve it, in order to eliminate the drawbacks arising therefrom, are insufficient. For example, a cylindrical lens is incorporated between the exit surface of the light-emitting means and the slit aperture. As a result, the illumination of the slit is no longer round, but instead is approximately oval or corresponds as much as possible to the slit shape. On the one hand, however, this action does not appreciably prevent the light loss, and on the other hand a cylindrical lens makes the light distribution in the slit inhomogeneous.

The inventor herein has recognized the problems of the approaches indicated above that attempt to increase the usable portion of the light. He has attempted, by way of the concept of the present invention, to achieve the most efficient possible light utilization in the slit image, while at the same time preventing absorption of the usable light on the slit aperture.

SUMMARY OF THE INVENTION

One object of the invention is therefore to create a slit lamp that avoids the disadvantages indicated above.

This object is achieved by an illumination apparatus comprising a light-emitting means for emitting an illumination beam having a round cross section, and at least one light-refracting optical element arranged on an optical axis of the illumination apparatus wherein the optical element has a light entrance surface and a light exit surface and wherein the optical element is equipped on at least one of the two surfaces with a free-form surface which is shaped so that in the operating state, all the light from the illumination beam is bundled into a resultant illumination beam having a triangular, rectangular, polygonal, semicircular, slit, or crescent-shaped cross section.

The use of a free-form surface (anisotropically curved surface) is advantageous where the free-form surface is arranged after the light-emitting means (e.g. a halogen lamp or an LED or a light guide exit surface) and possesses a particular property. A "free-form-surface lens" is to be understood for purposes of the invention as an optical component that permits target-oriented light guidance as a result of its conformation. It is to be understood in particular as a lens having a specifically configured surface topography which allows light rays that strike it to be conveyed in a desired direction that does not correspond to the direction resulting from imaging in accordance with a spherical lens.

The free-form surface allows not only a rotationally symmetrical deviation from the spherical, corresponding as a first approximation to an aspherical, but also any desired change in the radius of curvature with reference to every surface point on the lens surface. Whereas in previous imaging systems the imaging lenses produced round cross sections for the ray bundle of the illumination beam, with corresponding lenses having the novel free-form surfaces, the bundle cross section can be configured arbitrarily. It is thus possible, for example, to convert a round bundle cross section into a rectangular one. The conversion into the desired cross section does not occur directly at the exit surface of the free-form-surface lens; the light bundle forms only after exiting from the lens.

The optical element having the free-form surface is preferably a lens, but can also be a plate or a prism. All these optical elements have in common, according to the present invention, the fact that they receive the totality of the round cross section of the ray bundle. In the context of a lens or plate, this occurs in space-saving fashion with a correspondingly round light entrance surface.

The approaches known from the existing art generate a ray bundle that is rectangular in cross section by means of rectangular apertures or cylindrical lenses, by excluding a portion from the originally complete ray bundle that was round in cross section.

As a result, most of the light present is, not used. With a free-form-surface lens according to the present invention, on the other hand, the entire ray bundle, round in cross section, is always imaged. This can be accomplished using a rectangular light entrance surface (typical for plates or prisms) or, in space-saving fashion, with a round light entrance surface.

The free-form surface that describes the surface topography of such a lens can be represented by a higher-order (5th-order or higher) polynomial.

The configuration according to the present invention of a slit lamp that has been described comprises, in addition to the free-form-surface lens, a conventional slit aperture, although the latter could also be dispensed with. The slit aperture now no longer has the function of blocking off the round cross section of the illuminating ray bundle to yield a slit-shaped rectangular one, which would be associated with a large light loss. It serves only to generate contrast in, and to image in sharp-edged fashion, the rectangular cross section already produced by the free-form-surface lens.

In a refinement of this concept in the context of another embodiment of the slit lamp according to the present, invention having a correspondingly modified free-form surface, the use of the slit aperture can be dispensed with entirely. The surface topography of the free-form surface on the lens must then be configured so that it makes possible a sharp-edged, slit-shaped image of the cross section of the light bundle on the patient's eye. The slit-shaped image of the light bundle on the patient's eye then results exclusively from the surface conformation of the free-form surface of the lens.

The free-form-surface lens can have the free-form surface alternatively on the light entrance side, light exit side, or both sides.

A variant configuration according to the present invention provides that the free-form-surface lens, as well as the slit aperture, can be displaced along an axis of the illumination beam path.

A further variant configuration according to the present invention is designed for the most versatile possible application capability and for adaptation to different conditions. For that purpose, provision is made that the free-form-surface lens producing the rectangular ray bundle cross section can be rotated and/or also displaced along the optical axis of the slit lamp. The rotation thus allows, if necessary, not only a vertically oriented but also a horizontally or obliquely oriented, "light slit" to be generated. The displacement along the optical axis is used, when necessary, to pursue better focusing onto an imaging optic optionally located downstream. It is thereby also possible, however, to achieve the most accurate possible matching of the rectangular ray bundle cross section to the rectangular opening of the optionally arranged slit aperture, thereby attaining higher contrast in edge imaging. A displaceability of the slit aperture can, however, additionally be provided.

All current light-emitting means are possible for the slit lamp according to the present invention. These can be, for example, conventional incandescent lamps, light guides, or LEDs. The free-form-surface lens can be arranged in the immediate vicinity of the light-emitting means, or at a certain distance. Light-converging optical elements can also be arranged between the light-emitting means and the free-form surface. As a replacement or in combination, a concave mirror can also effect a bundling of the light emerging from the light-emitting means.

In a further variant according to the present invention, a free-form-surface lens is applied directly onto a glass body of the light-emitting means. Corresponding glass bodies can also be cast directly in one piece. In this case provision can be made for a displaceability and/or rotatability of the light-emitting means itself, for better focusing capability of the illumination beam.

The illumination apparatus described is, according to the present invention, combinable with a microscope in two ways: the illumination beam of modified cross section is introduced into the microscope by means of an optical reflecting-in element and is guided through the main objective; or it is directed onto the patient's eye from outside the microscope as oblique illumination. The latter variant embodiment is preferably configured so that the slit illumination can be pivoted aside or switched off as necessary. In a further preferred variant embodiment, the pivot apparatus therefor is configured so that pivoting can occur along a circular arc that is parallel to the stereo base of the microscope. This pivoting motion makes available to one skilled in the art a slit illumination with different angles of incidence onto the patient's eye, and ensures, for example, the ability to diagnose opacities in the transparent media of the patient's eye.

When the slit illumination device according to the present invention is combined with a microscope, in particular a surgical microscope, it can be switched in as desired and when necessary. In order, however, to make superfluous a further conventional illumination system of the microscope, the slit illumination apparatus according to the present invention is configured in such a way that the optical element having a free-form surface that generates the light slit can be switched in. When it is introduced into the illumination beam path, the observer then sees only the light slit on the patient's eye for diagnostic purposes; and when the optical element is not switched in, a microscope illumination with a full cross section is then available to the observer.

BRIEF DESCRIPTION OF THE DRAWINGS

The invention will be explained, symbolically and by way of example, with reference to Figures.

The Figures are described in continuous and overlapping fashion. Identical reference characters denote identical components; reference characters having different indices indicate identically functioning or similar components.

In the drawings, schematically in each case:

FIG. 1 shows a slit lamp according to the existing art;

FIG. 2 depicts, as an example, a lens having a free-form surface;

FIG. 3 depicts, as an example, the mode of operation of a lens having a free-form surface;

FIG. 3a shows a round cross section of an illumination beam;

FIG. 3b shows a rectangular cross section of a resultant illumination beam;

FIG. 4 shows an illumination apparatus according to the present invention in the form of a slit lamp having a, slit aperture and an imaging optic;

FIG. 5 shows a variant configuration of an illumination apparatus according to the present invention in the form of a slit lamp;

FIG. 6 shows an illumination apparatus according to the present invention that is combined with a microscope, wherein the illumination apparatus is selectably operable as a slit lamp having a slit-shaped resultant illumination beam or as an illumination system having a conventional illumination beam;

FIG. 7 shows an assemblage according to the present invention of a microscope having an illumination apparatus that can be pivoted in, in the form of a slit lamp; and FIG. 8 shows a light-emitting means having a free-form lens.

DETAILED DESCRIPTION OF THE INVENTION

Figure 1:
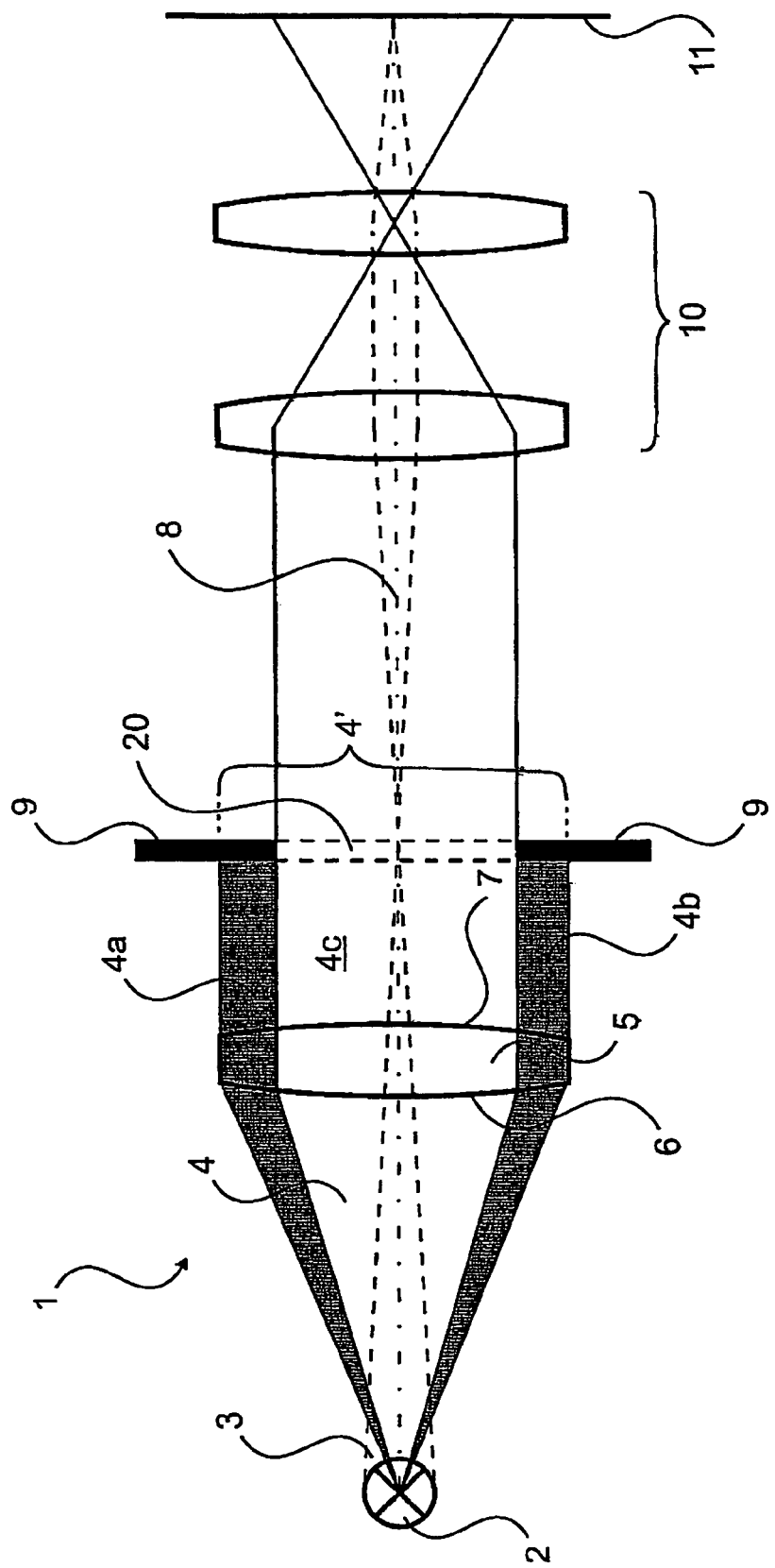

FIG. 1 is a longitudinally sectioned depiction of an illumination apparatus 1 that is used according to the existing art as a slit lamp. Here a light-emitting means 2 generates an image beam 3 and an illumination beam 4 which proceed along an optical axis 8. These two beam strike an optical element 5 (usually a converging lens) that has a light entrance surface 6 and a light exit surface 7. Optical element 5 bundles illumination beam 4 onto a slit aperture 9 that has a slit-shaped opening 20. As a result, only the light bundle of illumination beam 4 corresponding to slit aperture opening 20 can now pass through slit aperture 9. Resultant illumination beam 4' is thus made up of an actually utilized portion 4c of illumination beam 4, and two (in this sectioned depiction) unutilized portions 4a and 4b that are absorbed by slit aperture 9 and converted into heat. The slit-shaped light beam that thus remains is then imaged by an imaging optic 10 onto illuminated plane 11, which as a rule, in the context of an application as a slit lamp, is a patient's eye. This conventional slit lamp technique is associated with poor light utilization and considerable heating.

Figure 2:
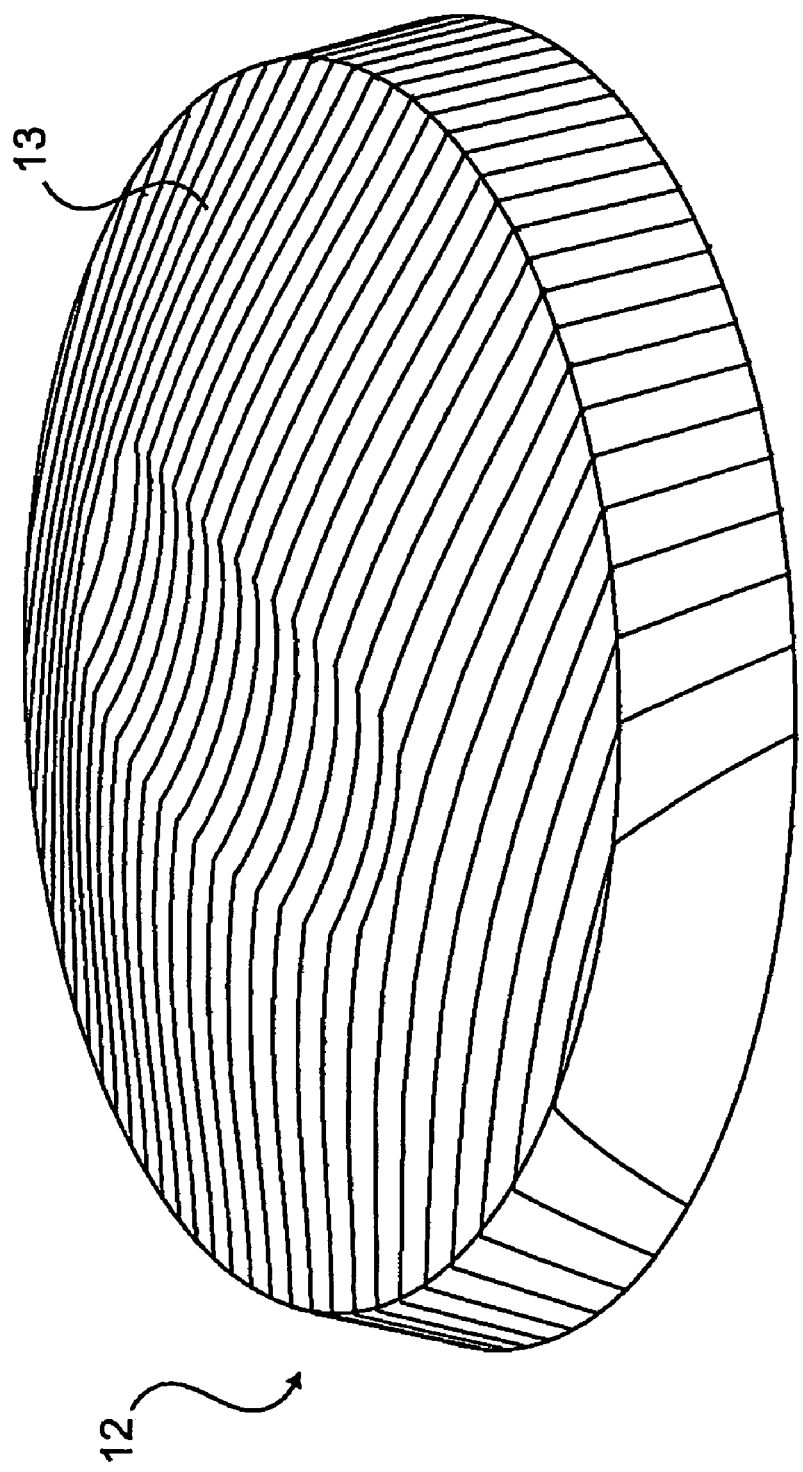

FIG. 2 shows, as an example, a free-form-surface lens 12 that has a free-form surface 13. The latter is depicted as an irregular surface deviating from a sphere.

FIG. 3 shows the mode of operation of a free-form-surface lens 12 having a free-form surface 13 that receives an illumination beam 4 from a light-emitting means 2. Light entrance surface 6 is embodied in conventionally spherical fashion, and light exit surface 7 is configured as free-form surface 13. Illumination beam 4 has a round cross section 14 (section A-A in FIG. 3a), and resultant illumination beam 4' has a rectangular or slit-shaped cross section 15 (section B-B in FIG. 3b).

Figure 4:
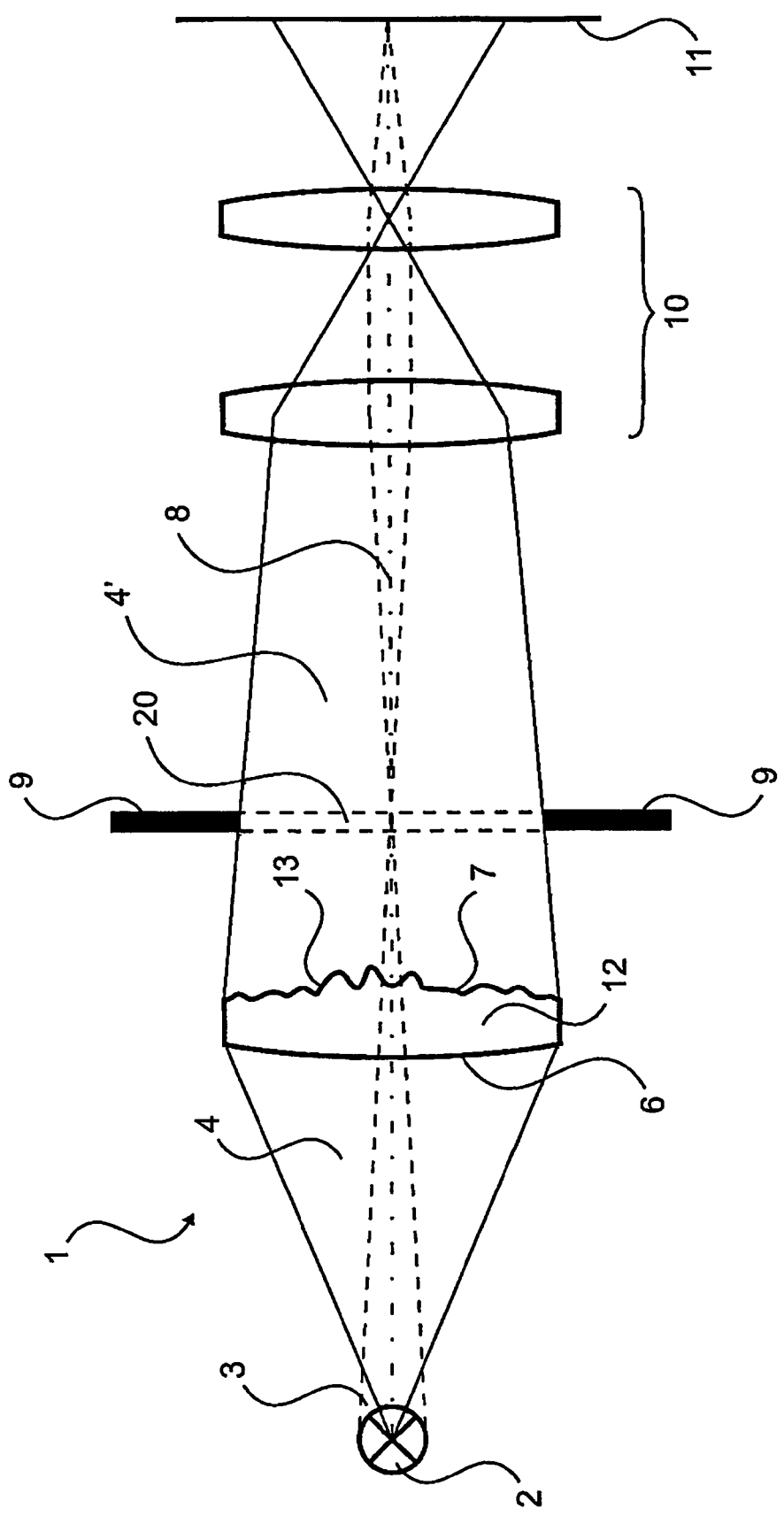

FIG. 4 shows the use according to the present invention, in an illumination apparatus or slit lamp 1, of a free-form-surface lens 12 whose light exit surface 7 is configured as free-form surface 13. Although the provision of a slit aperture 9 is now no longer necessary, because resultant illumination beam 4' already has a slit-shaped cross section, such an aperture is provided for better contouring of the slit-shaped beam.

Figure 5:
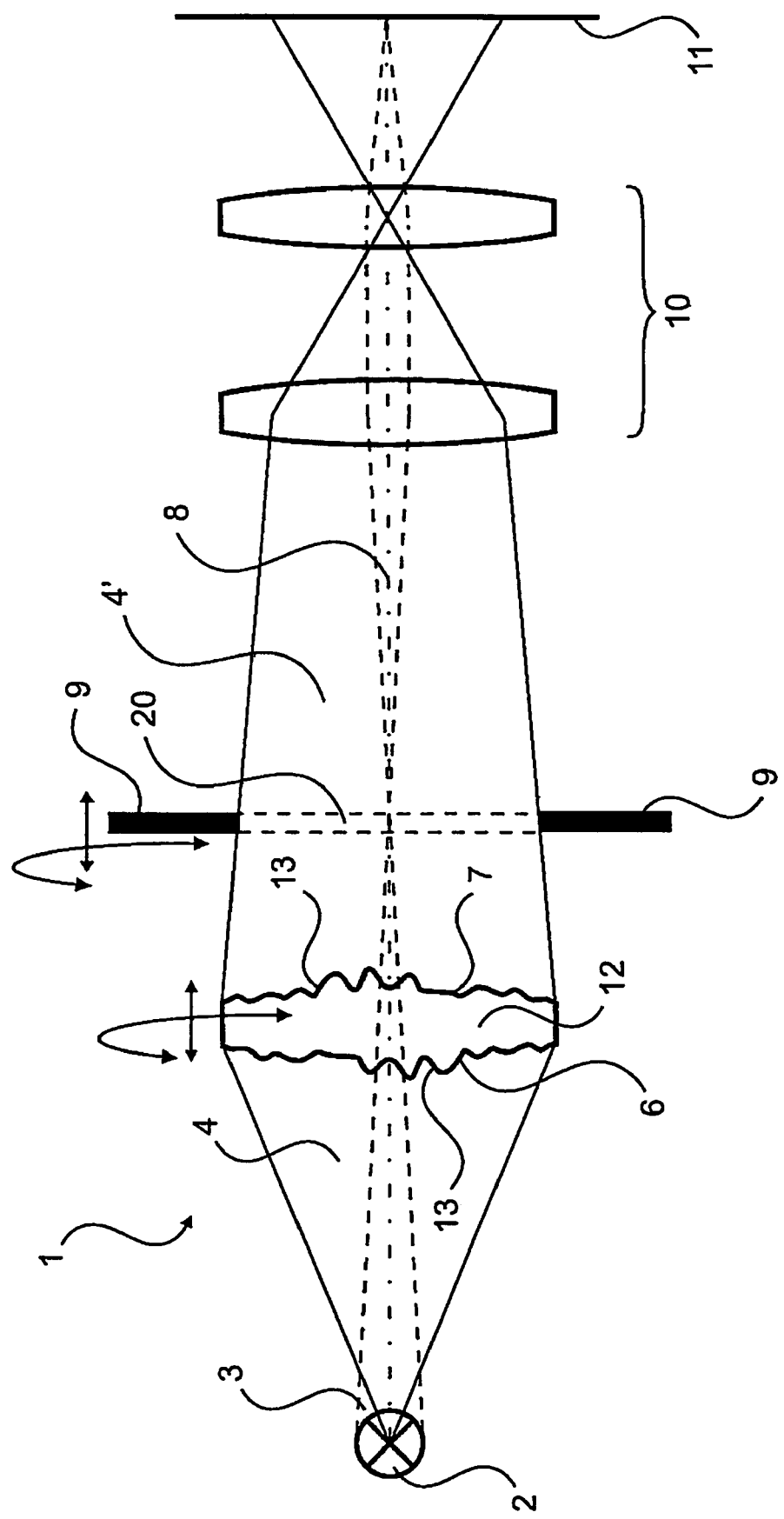

FIG. 5 shows a further variant configuration according to the present invention of an illumination apparatus 1 having a free-form-surface lens 12 that comprises a free-form surface 13 on both light, entrance surface 6 and light exit surface 7. In addition, both free-form-surface lens 12 and slit aperture 9 are arranged displaceably along optical axis 8 and rotatably thereabout. The contour, position, and light intensity of the light slit imaged onto illuminated plane (patient's eye) 11 can thereby be influenced.

Figure 6:
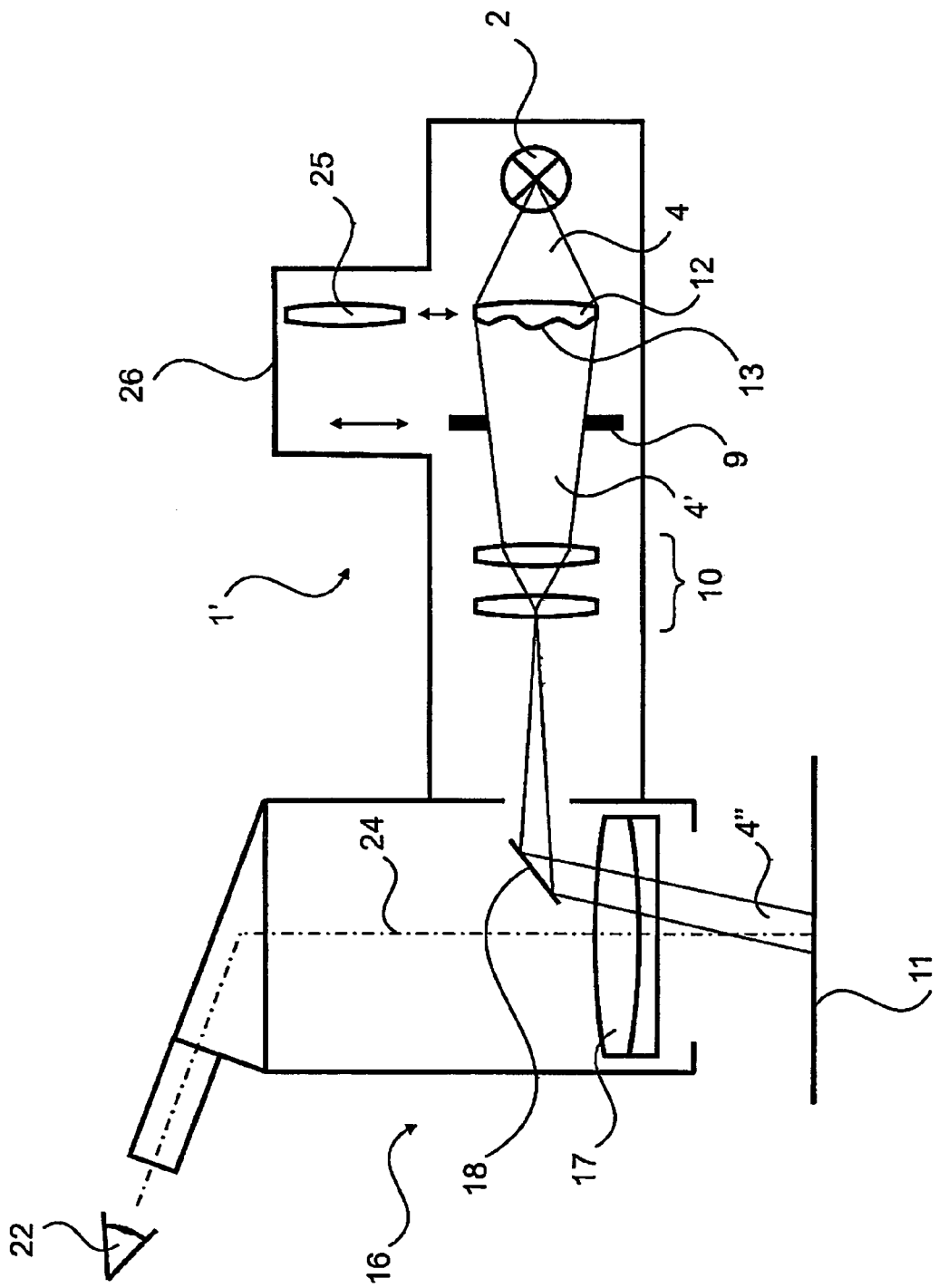

FIG. 6 shows a combination according to the present invention of a newly introduced illumination apparatus or slit lamp 1 with a microscope 16. The slit lamp is arranged on microscope 16 in such a way that the slit-shaped beam is directed by a reflecting-in element 18 through a main objective 17 onto the illuminated plane or patient's eye 11. Reflecting-in element 18 can be oriented in such a way that resultant illumination beam 4' illuminates the center of the microscope's visual field, that center being located around an optical axis 24 of microscope 16. This variant configuration furthermore comprises an interchange apparatus 26 which allows slit aperture 9 to be displaced or pivoted, and also allows free-form-surface lens 12 to be interchanged in similar fashion with a conventionally shaped replacement lens 25. As a result, illumination apparatus 1' is usable selectably as a conventional microscope illumination system or as a slit lamp.

FIG. 7 shows an illumination apparatus or slit lamp 1 that can be pivoted in or out as necessary by means of a pivot apparatus 23. Pivot apparatus 23 makes two different pivoting directions available. One pivoting motion proceeds about articulation 28, and serves to switch the slit illumination in or out. The second pivoting direction proceeds about pivot axis 27, i.e. parallel to the stereo base of microscope 16. The latter pivoting motion is important for diagnostic purposes, and known to one skilled in the art.

FIG. 8 shows a light-emitting means 2 that is equipped directly with a free-form-surface lens 12. A combination of the two could also be embodied in one-piece fashion. A concave mirror 19 ensures that a portion of light emerging to the left is also conveyed to free-form-surface lens 12.

What is claimed is:

1. An illumination apparatus comprising:
    a light-emitting means for emitting an illumination beam having a round cross section; and
    a light-refracting optical element arranged to receive the illumination beam, wherein the optical element includes a light entrance surface and a light exit surface, at least one of the light entrance surface and the light exit surface having a free-form surface shaped so that all the light from a received illumination beam is bundled into a resultant illumination beam having a cross-sectional shape chosen from a group of shapes consisting of a triangle, a rectangle, a polygon, a semicircle, a slit, and a crescent;
    wherein the optical element is rotatable about an optical axis of the illumination beam, an imaging optic is arranged after the optical element on the optical axis, the optical element is arranged directly on the light-emitting means, and the light-emitting means and optical element are displaceable along the optical axis.

2. The illumination apparatus as defined in claim 1, wherein the light-emitting means includes a transparent body, and the optical element and transparent body are configured in one piece.

3. An illumination apparatus comprising:
    a light-emitting means for emitting an illumination beam having a round cross section; and
    a light-refracting optical element arranged to receive the illumination beam, wherein the optical element includes a light entrance surface and a light exit surface, at least one of the light entrance surface and the light exit surface having a free-form surface shaped so that all the light from a received illumination beam is bundled into a resultant illumination beam having a cross-sectional shape chosen from a group of shapes consisting of a triangle, a rectangle, a polygon, a semicircle, a slit, and a crescent;
    wherein the optical element is rotatable about an optical axis of the illumination beam, an imaging optic is arranged after the optical element on the optical axis, the optical element is arranged directly on the light-emitting means, and the light-emitting means and optical element are rotatable about the optical axis.

4. An illumination apparatus comprising:
a light-emitting means for emitting an illumination beam having a round cross section;
a light-refracting optical element arranged to receive the illumination beam, wherein the optical element includes a light entrance surface and a light exit surface, at least one of the light entrance surface and the light exit surface having a free-form surface shaped so that all the light from a received illumination beam is bundled into a resultant illumination beam having a cross-sectional shape chosen from a group of shapes consisting of a triangle, a rectangle, a polygon, a semicircle, a slit, and a crescent;
wherein the free-form surface is describable by a 5th-order or higher polynomial.

5. A microscope comprising:
a main objective;
a light-emitting means for emitting an illumination beam having a round cross section;
a light-refracting optical element arranged to receive the illumination beam, wherein the optical element includes a light entrance surface and a light exit surface, at least one of the light entrance surface and the light exit surface having a free-form surface shaped so that all the light from a received illumination beam is bundled into a resultant illumination beam having a cross-sectional shape chosen from a group of shapes consisting of a triangle, a rectangle, a polygon, a semicircle, a slit, and a crescent; and
a reflecting element arranged to redirect the resultant illumination beam through the main objective to illuminate an object plane; and
an interchange apparatus for selectably positioning either the optical element or a conventionally shaped lens to receive the illumination beam, whereby a slit-lamp diagnostic mode and a standard illumination mode are selectable by a user.

* * * * *